US008043300B2

(12) United States Patent
Madden et al.

(10) Patent No.: US 8,043,300 B2
(45) Date of Patent: Oct. 25, 2011

(54) HANDPIECE TIP ASSEMBLY

(75) Inventors: Sean C. Madden, Mission Viejo, CA (US); John M. Bourne, Torrance, CA (US)

(73) Assignee: Alcon, Inc., Hunenberg (CH)

( * ) Notice: Subject to any disclaimer, the term of this patent is extended or adjusted under 35 U.S.C. 154(b) by 656 days.

(21) Appl. No.: 11/174,772

(22) Filed: Jul. 5, 2005

(65) Prior Publication Data

US 2007/0016222 A1 Jan. 18, 2007

(51) Int. Cl.
*A61F 9/00* (2006.01)
(52) U.S. Cl. .......................... 606/107; 604/263; 206/438
(58) Field of Classification Search .................... 604/22, 604/27, 506, 513, 162, 164.07, 164.08, 192, 604/240, 111, 263; 606/166–169, 107, 159; 206/438
See application file for complete search history.

(56) References Cited

U.S. PATENT DOCUMENTS

| | | | |
|---|---|---|---|
| 1,667,273 A | 4/1928 | Stewart | |
| 2,371,086 A | 3/1945 | Watson et al. | |
| 2,836,942 A * | 6/1958 | Miskel | 53/425 |
| 2,896,622 A | 7/1959 | Huttermann | |
| 2,935,067 A | 5/1960 | Bouet | |
| 2,953,243 A | 9/1960 | Roehr | |
| 3,073,307 A * | 1/1963 | Stevens | 604/192 |
| 3,215,141 A | 11/1965 | Podhora | |
| 3,523,530 A | 8/1970 | Pagones et al. | |
| 4,022,191 A | 5/1977 | Jamshidi | |
| 4,334,536 A | 6/1982 | Pfleger et al. | |
| 4,496,352 A | 1/1985 | Soika | |
| 4,576,164 A | 3/1986 | Richeson et al. | |
| 4,646,722 A * | 3/1987 | Silverstein et al. | 600/104 |
| 4,720,285 A | 1/1988 | Pickhard | |
| 4,735,618 A | 4/1988 | Hagen | |
| 4,747,829 A * | 5/1988 | Jacob et al. | 604/110 |
| 5,219,339 A | 6/1993 | Saito | |
| 5,255,804 A * | 10/1993 | Butterbrodt | 604/111 |
| 5,312,413 A | 5/1994 | Eaton et al. | |
| 5,344,404 A * | 9/1994 | Benson | 604/110 |
| 5,344,408 A * | 9/1994 | Partika | 604/192 |
| D354,283 S | 1/1995 | Rhen, Jr. et al. | |
| 5,616,120 A | 4/1997 | Andrew et al. | |
| D381,421 S | 7/1997 | Casica et al. | |
| 5,702,270 A | 12/1997 | Casica et al. | |
| D397,433 S | 8/1998 | Casica et al. | |
| 5,910,132 A | 6/1999 | Schultz | |
| 5,913,868 A | 6/1999 | Marshall et al. | |
| 5,916,149 A | 6/1999 | Ryan | |
| 5,968,021 A | 10/1999 | Ejlersen | |
| 5,980,495 A | 11/1999 | Heinz | |

(Continued)

FOREIGN PATENT DOCUMENTS

DE 29718021 U1 11/1997

(Continued)

OTHER PUBLICATIONS

International Searching Authority, Written Opinion of the International Searching Authority, PCT/US 06/024900, Jan. 5, 2008, 5 pages.

*Primary Examiner* — Theodore Stigell

(57) ABSTRACT

A tip assembly for a liquefaction surgical handpiece having a break-away or frangible tip protector. The tip protector protects the delicate tip from damage during handling and shipment, but is easily removed prior to use.

7 Claims, 1 Drawing Sheet

U.S. PATENT DOCUMENTS

| | | | |
|---|---|---|---|
| 5,989,212 A | 11/1999 | Sussman et al. | |
| 5,997,499 A | 12/1999 | Sussman et al. | |
| 6,053,892 A * | 4/2000 | Meyer | 604/110 |
| 6,080,128 A | 6/2000 | Sussman et al. | |
| 6,110,162 A | 8/2000 | Sussman et al. | |
| 6,179,805 B1 | 1/2001 | Sussman et al. | |
| 6,206,848 B1 | 3/2001 | Sussman et al. | |
| 6,254,530 B1 * | 7/2001 | Ryan, Jr. | 600/177 |
| 6,716,199 B2 | 4/2004 | DeHarde et al. | |
| 7,169,134 B2 * | 1/2007 | Bills | 604/236 |
| 2003/0187407 A1 * | 10/2003 | Bills | 604/236 |
| 2003/0229316 A1 | 12/2003 | Hwang et al. | |
| 2004/0024380 A1 | 2/2004 | Darnell | |

FOREIGN PATENT DOCUMENTS

| | | |
|---|---|---|
| EP | 0276160 A3 | 7/1988 |
| EP | 0276160 B1 | 7/1988 |
| EP | 0 747 085 | 3/2000 |
| EP | 0747085 B2 | 4/2003 |
| GB | 225154 | 11/1924 |
| GB | 1555391 | 11/1979 |
| WO | WO 00/16832 A1 | 3/2000 |
| WO | WO 2007/005397 A1 | 1/2007 |

* cited by examiner

HANDPIECE TIP ASSEMBLY

BACKGROUND OF THE INVENTION

This invention relates generally to the field of cataract surgery and more particularly to a tip assembly for use on a liquefaction handpiece.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution and the introduction of a relatively cool irrigating solution, thereby quickly cooling and removing the heated solution. This technique is more fully described in U.S. Pat. No. 5,616,120 (Andrew, et al.), the entire contents of which is incorporated herein by reference.

Handpiece and tips suitable for practicing this technique are described in U.S. Pat. Nos. 5,989,212, 5,997,499, 6,080, 128, 6,110,162, 6,179,805 and 6,206,848 (Sussman, et al.), the entire contents of which being incorporated herein by reference. These patents do not disclose any details on how to protect the tip from damage.

Therefore, a need continues to exist for an assembly for protecting a handpiece tip.

BRIEF SUMMARY OF THE INVENTION

The present invention improves upon the prior art by providing a tip assembly for a liquefaction surgical handpiece having a break-away or frangible tip protector. The tip protector protects the delicate tip from damage during handling and shipment, but is easily removed prior to use.

Accordingly, one objective of the present invention is to provide a tip assembly for a liquefaction surgical handpiece.

Another objective of the present invention is to provide a tip assembly having a tip protector.

These and other advantages and objectives of the present invention will become apparent from the detailed description and claims that follow.

DETAILED DESCRIPTION OF THE INVENTION

Figure 1:
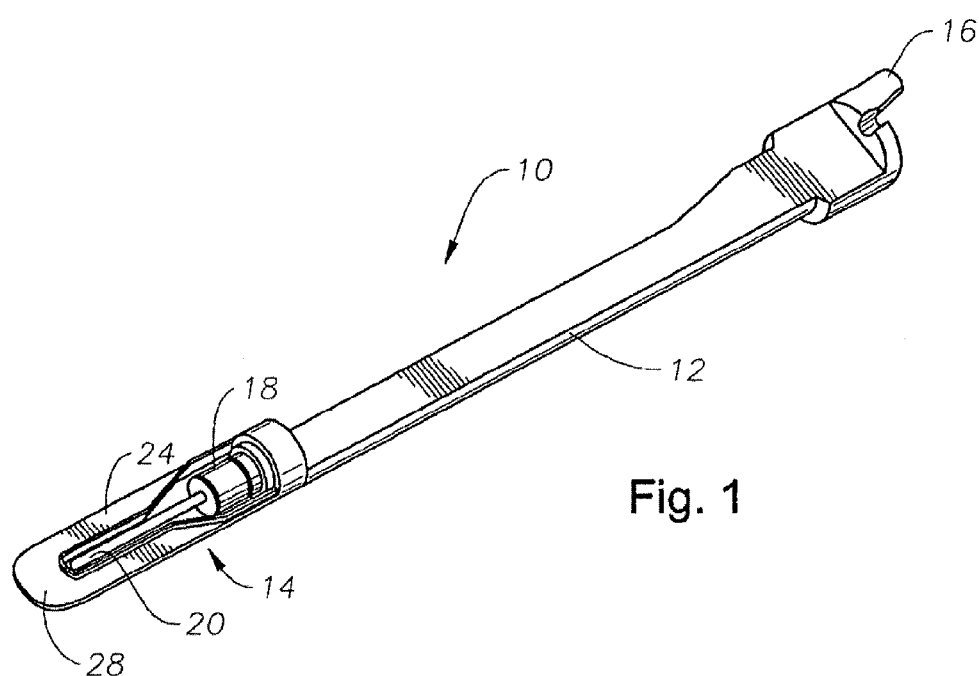
FIG. 1 is a perspective view of a handpiece having the tip assembly of the present invention.
Figure 2:
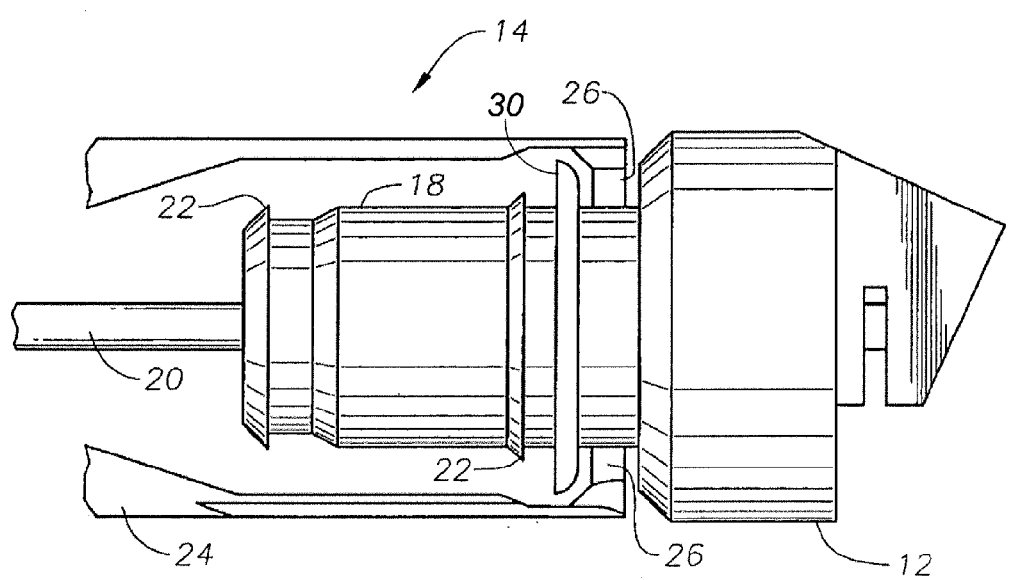
FIG. 2 is an exploded perspective view of the tip assembly of the present invention.

As best seen in FIG. 1, handpiece 10 that may be used with the tip assembly of the present invention generally include body 12 with tip assembly 14 located at the distal end of body 12 and at least one fitting 16 for connection to a source of irrigation and/or aspiration. As best seen in FIG. 2, tip assembly 14 generally contains hub 18 that is connected to or integrally molded with body 12. Hub 18 is generally hollow and is sized and shaped to telescopically receive tip 20. Hub 18 may also contain flanges 22, for receiving and retaining an infusion sleeve (not shown), and a third flange 30. Tip assembly 14 also contains tip protector 24, which is connected to hub 18 by break-away or frangible connectors 26. Tip protector 24 is sized and shaped to project away from hub 18 and around tip 20 so as to protect tip 20 from damage during shipment and handling. Tip protector 24 preferably contains flattened, enlarged grasping portion 28 allowing tip protector 24 to be more easily removed from hub 18. Hub 18 and tip protector 24 may be integrally molded from any suitable material, such as a thermoplastic.

This description is given for purposes of illustration and explanation. It will be apparent to those skilled in the relevant art that changes and modifications may be made to the invention described above without departing from its scope or spirit.

We claim:

1. A surgical handpiece, comprising:
   a liquefaction handpiece body, comprising a fitting for connection to a source of aspiration;
   a phacoemulsification tip received in a hollow hub sized and shaped to telescopically receive the phacoemulsification tip, the hub being connected to the body;
   a flange located on the hub, wherein the flange is configured to retain an infusion sleeve; and
   a tip protector integrally molded with and connected to the hub by at least one frangible connector, wherein the at least one frangible connector is attached to the hub between where the hub connects to the needle and where the hub is connected to the liquefaction body;
   wherein the attached tip protector projects away from the hub, over the flange, and around the tip so as to protect the tip from damage during shipment and handling;
   wherein the tip protector is configured to be removed prior to using the tip as the tip is configured to be used with the tip protector removed from the tip;
   wherein the tip protector contains a flattened grasping portion;
   wherein the flange is a first flange, and wherein the hub further comprises a second flange, wherein the first flange and the second flange are configured to retain an infusion sleeve and wherein the at least one frangible connector is attached to the hub between the liquefaction body and the flange closest to the liquefaction body.

2. The surgical handpiece of claim 1, wherein the flattened grasping portion is configured to be removed by grasping the flattened grasping portion of the tip protector, applying a force to the tip protector through the flattened grasping portion to break the at least one frangible connector, and removing the tip protector from the tip.

3. The surgical handpiece of claim 1, wherein the hub comprises a third flange with a radius that is greater than the first flange and the second flange, and wherein the third flange is located between the liquefaction body and the first or second flange closest to the liquefaction body.

4. The surgical handpiece of claim 3, wherein the at least one frangible connector is attached to the hub between the liquefaction body and the third flange.

5. The surgical handpiece of claim 3, wherein the tip protector extends over the third flange.

6. The surgical handpiece of claim 1, wherein the tip protector extends around a portion of the hub configured to secure an infusion sleeve such that when the tip protector is removed, the portion of the hub configured to secure an infusion sleeve is exposed.

7. The surgical handpiece of claim 1, wherein an overall width of the tip protector is substantially the same as an overall width of the handpiece body.

\* \* \* \* \*